United States Patent
Fuchs et al.

(10) Patent No.: US 6,514,544 B2
(45) Date of Patent: Feb. 4, 2003

(54) BEVERAGE FOR INCREASING THE BODY'S CAPACITY TO BREAK DOWN ALCOHOL AND METHOD THEREOF

(75) Inventors: Norbert Fuchs, Unternberg (AT); Reinhard Wallner, Unternberg (AT)

(73) Assignee: JHS-Privatstiftung, Bruck (AT)

( * ) Notice: Subject to any disclaimer, the term of this patent is extended or adjusted under 35 U.S.C. 154(b) by 0 days.

(21) Appl. No.: 09/861,395

(22) Filed: May 18, 2001

(65) Prior Publication Data

US 2001/0033881 A1 Oct. 25, 2001

Related U.S. Application Data

(63) Continuation of application No. PCT/AT99/00282, filed on Nov. 19, 1999.

(30) Foreign Application Priority Data

Nov. 19, 1998 (AT) .............................. 1934/98

(51) Int. Cl.⁷ .............................. A23L 1/302; A23L 2/38
(52) U.S. Cl. .......................... 426/72; 426/74; 426/590; 426/591; 426/656; 426/658
(58) Field of Search .............................. 426/590, 72, 74, 426/591, 656, 658

(56) References Cited

FOREIGN PATENT DOCUMENTS

| | | |
|---|---|---|
| CN | 1090146 A | 8/1994 |
| CN | 1126588 | 7/1996 |
| DE | 19720818 | 5/1998 |
| EP | 0583852 | 2/1994 |
| EP | 0652012 | 5/1995 |
| JP | 61162159 A | 7/1986 |
| JP | 2713392 | 8/1995 |
| JP | 8-73350 | 3/1996 |
| KR | 9500456 B1 | 1/1995 |
| WO | WO 8701285 | 3/1987 |
| WO | WO 9702830 | 1/1997 |

*Primary Examiner*—Helen Pratt
(74) *Attorney, Agent, or Firm*—Fulbright & Jaworski L.L.P.

(57) ABSTRACT

A fructose-containing refreshing drink composition for increasing the alcohol degradation capacity of the body is provided which contains one or more components of the vitamin B complex as well as taurine; furthermore, a refreshing drink, a syrup as well as a dry substance for increasing the alcohol degradation capacity are provided.

57 Claims, 6 Drawing Sheets

| TIME | PER MILL | BEVERAGE |
|---|---|---|
| 0 | 0 | C |
| 0 : 25 | 0 , 05 | B |
| 0 : 50 | 0 , 29 | B |
| 1 : 15 | 0 , 42 | B |
| 1 : 30 | 0 , 36 | C |
| 1 : 55 | 0 , 37 | S |
| 2 : 17 | 0 , 58 | W |
| 2 : 45 | 0 , 69 | S |
| 3 : 05 | 0 , 82 | C |
| 3 : 22 | 0 , 89 | S |
| 3 : 45 | 1 , 1 | S |
| 4 : 15 | 0 , 95 | M |
| 5 : 00 | 1 , 02 | C |
| 5 : 20 | 0 , 87 | - |
| 5 : 35 | 0 , 88 | - |

FIG. 1

| TIME | PER MILL | BEVERAGE |
|---|---|---|
| 0 | 0 | C |
| 0:25 | 0,05 | B |
| 0:52 | 0,21 | B |
| 1:20 | 0,49 | B |
| 1:35 | 0,42 | C |
| 1:57 | 0,42 | S |
| 2:20 | 0,56 | B |
| 2:48 | 0,75 | S |
| 3:10 | 0,69 | C |
| 3:30 | 0,86 | S |
| 3:55 | 1,05 | S |
| 4:20 | 1,13 | B |
| 5:00 | 1,13 | C |
| 5:25 | 1,12 | - |

FIG. 2

| TIME | PER MILL | BEVERAGE |
|------|----------|----------|
| 0    | 0        | C        |
| 0:25 | 0,05     | B        |
| 0:54 | 0,14     | B        |
| 1:20 | 0,27     | B        |
| 1:35 | 0,29     | C        |
| 1:55 | 0,31     | S        |
| 2:22 | 0,41     | B        |
| 2:51 | 0,54     | S        |
| 3:15 | 0,55     | C        |
| 3:30 | 0,57     | S        |
| 3:48 | 0,69     | S        |
| 4:05 | 0,91     | B + TOAST |
| 5:05 | 0,84     | C        |
| 5:30 | 0,83     | -        |

FIG. 3

| TIME | PER MILL | BEVERAGE |
|------|----------|----------|
| 0    | 0        | I        |
| 0:20 | 0,16     | B        |
| 0:45 | 0,26     | B        |
| 1:15 | 0,34     | B        |
| 1:30 | 0,30     | I        |
| 1:50 | 0,32     | S        |
| 2:23 | 0,42     | B        |
| 2:40 | 0,5      | S        |
| 3:00 | 0,45     | I        |
| 3:25 | 0,51     | S        |
| 3:45 | 0,71     | S        |
| 4:10 | 0,89     | B        |
| 4:40 | 0,72     | I        |
| 4:55 | 0,66     | -        |
| 5:00 | 0,63     | I        |
| 5:20 | 0,63     | -        |

FIG. 4

| TIME | PER MILL | BEVERAGE |
|---|---|---|
| 0 | 0 | I |
| 0:30 | 0,13 | B |
| 0:55 | 0,25 | B |
| 1:20 | 0,32 | B |
| 1:37 | 0,22 | I |
| 1:55 | 0,22 | S |
| 2:30 | 0,31 | W |
| 2:45 | 0,32 | S |
| 3:05 | 0,31 | I |
| 3:28 | 0,37 | S |
| 3:55 | 0,48 | S |
| 4:30 | 0,53 | B |
| 4:48 | 0,46 | I + TOAST |
| 5:05 | 0,40 | – |
| 5:20 | 0,34 | – |

FIG. 5

| TIME | PER MILL | BEVERAGE |
|------|----------|----------|
| 0    | 0        | I        |
| 0:20 | 0        | B        |
| 0:50 | 0,19     | B        |
| 1:20 | 0,30     | B        |
| 1:25 | 0,21     | I        |
| 1:30 | 0,27     | S        |
| 2:20 | 0,31     | W        |
| 2:40 | 0,34     | S        |
| 2:45 | 0,36     | I        |
| 3:20 | 0,38     | S        |
| 3:45 | 0,41     | S        |
| 4:15 | 0,60     | B        |
| 4:50 | 0,79     | I        |
| 4:55 | 0,57     | I        |
| 5:00 | 0,69     | I        |
| 5:15 | 0,57     | -        |

FIG. 6

BEVERAGE FOR INCREASING THE BODY'S CAPACITY TO BREAK DOWN ALCOHOL AND METHOD THEREOF

This application is a continuation of PCT Application No. PCT/AT99/00282 filed Nov. 19, 1999, which claims priority to Austrian Application No. A 1934/98 filed Nov. 19, 1998.

The invention relates to a fructose-containing refreshing drink composition for increasing the alcohol degradation capacity of the body.

The invention further relates to a refreshing drink, a syrup as well as a dry substance for increasing the alcohol degradation capacity of the body.

The resorption of alcohol (ethanol) is effected both from the stomach and from the intestines. As a rule, the resorption is completed within approximately one hour, in the sober state, however, somewhat earlier, and it may be somewhat delayed in case the stomach/intestines is (are) very full. Based on the oil/water distribution quotient of 0.04, the alcohol is rapidly distributed within the body fluid. Because of this rapid concentration equalization, the alcohol level in blood is considered to be representative of the concentration of the alcohol in the central nervous system (CNS), the essential site of effect.

Approximately 2–3% of the reabsorbed alcohol are excreted via the lungs, approximately 1–2% via the kidneys. The main amount, however, is metabolized in the liver. When this occurs, ethyl alcohol is oxidized by alcohol-dehydrogenase (ADH) to acetaldehyde. The enzyme ADH carries zinc as catalytic center and is NADH-dependent. Besides this, however, small portions of the alcohol are also oxidized to acetaldehyde and acetic acid, respectively, via the P450-dependent enzyme system of the monooxygenases. Slight amounts (0.5%) are directly glucuronated, traces are coupled to sulfuric acid and excreted with the urine. The acetaldehyde formed by ADH is further oxidized to acetic acid by the enzyme aldehyde-dehydrogenase. The acetic acid thus incurred is partly used in the intermediary metabolism via activation of coenzyme A, yet the major portion of the acetic acid is cleaved in the tricarboxylic acid cylcle into $CO_2$ and $H_2O$. One gram of ethanol yields 7.1 kcal (approximately 30 kJ) and thus may also serve as partial energy source.

A refreshing drink for lowering the alcohol level in blood has been described in EP 0 205 634 A or in DE-C1 4 431 178, and it contains water, fructose, ascorbic acid and flavoring agents and/or citric acid and/or quinine. The alcohol degradation-accelerating activity of fructose has long been known, the addition of ascorbic acid (vitamin C) acts degradation-promoting.

Furthermore, a beverage for accelerating the degradation of alcohol within the body is known from the article "Alko-Killer", p. 44 of the periodical "PRAXIS", No. 8–9/98. In addition to fructose and vitamin C, this beverage contains the coenzymes AND+/NADH (nicotinamide-adenine-dinucleotide). AND+/NADH are coenzymes to which the hydrogen is transferred which forms during the oxidation of ethanol to acetaldehyde by the alcohol-dehydrogenase. Alcohol-dehydrogenase is an enzyme which metabolizes in the liver 90% of the ethanol consumed. By the addition of the coenzymes AND+/NADH to the beverage, the content of these coenzymes rises in the body by consuming the beverage, and thus also the alcohol degradation rate increases. What is disadvantageous in this connection is that AND+ is decomposed, even at 4° C., and NADH is decomposed in acidic and aqueous solutions to form dehydrogenase inhibitors, which, however, interferes with the alcohol degradation in the liver. So, if this drink is stored for an extended period of time (even at 4° C. in the refrigerator), it loses its activity or may even have an opposite effect.

WO 87 01285 A discloses a therapeutical composition for the treatment of acute and/or chronic symptoms occurring in connection with excessive alcohol consumption. This composition comprises an analgesic as well as nicotin amide and/or AND. The composition optionally may also comprise fructose, water-soluble vitamins, an antazide, an electrolyte substitue, such as potassium, sodium, magnesium or calcium, trace metals, such as zinc ions, an antihistaminic component, alkaloids, caffeine and further additives, such as flavoring agents and sweeteners. For the effect of the composition it is of particular importance that the nicotinic amide and the AND, respectively, be added to at least 7% by weight of the analgesics. Analgesics are pain killers, the more potent ones being potentially addictive for patients, and the weaker analgesics causing side reactions, such as reducing the production of the mucosa of the stomach and of the intestines. The ingestion of a composition having relatively strong side effects is not suitable for treating symptoms of an excessive alcohol consumption, and in persons who frequently take this composition it may cause damage to their health.

CN 1 090 146 A discloses a health drink which, i.a., comprises water-soluble vitamin B, fructose, trace elements, vitamin A, vitamin C, amino acids and counteracts the residual toxicity of alcohol.

In KR 9 500 456 B1 a beverage against the effects of alcohol has been described, this beverage i.a. comprising 1–10% of fructose and 0.05–0.5% of vitamin B2 as well as a filtrate of a fermentation with lactiacid-producing bacteria. Fermentation is performed under special conditions (30–40° C., pH 9–9.5, 50–100 h). The production of this beverage is comparatively complex, which as a rule will also affect the price of the beverage.

JP 61162159 A discloses a beverage for accelerating the reduction of alcohol in blood, the beverage comprising fructose, vitamin c and quinine or quinine derivatives.

Therefore, it is an object of the present invention to provide a refreshing drink composition which markedly accelerates the alcohol degradation rate within the body—also as compared to fructose (vitamin C) mixtures, without, however, adding enzymes or NADH+/AND, respectively, so that thus the useful life of the product will not be restricted. Furthermore, the composition shall not comprise any substances that cause side effects damaging health by a frequent consumption thereof. A further object of the present invention is to provide a refreshing drink, a syrup and a dry substance having these properties.

The refreshing drink composition of the initially defined kind is characterized in that it comprises one or more components of the vitamin B complex as well as taurine in addition to fructose. Surprisingly, in this manner the rate of the alcohol degradation within the body can very effectively be increased, preferably by at least 45% (cf. the examples). The fructose added may be provided in any form known, and it may also be phosphorylated. The composition according to the invention has a high stability and thus is storable over an extended period of time.

As the vitamin B complex, all water-soluble vitamins with the exception of vitamin C are defined. In many cases, they are components of coenzymes (cf. below) which are active in redox reactions and thus directly and indirectly promote the reaction of the alcohol dehydrogenase. Particularly the activation of the tricarboxylic acid cycle by the vitamins of the B complex is an essential characteristic of the present invention, because it has been found that by the activation of the citrate cycle also the alcohol degradation rate can decisively be increased.

Taurine is the name of 2-aminoethane sulfonic acid, and it occurs in nearly all mammal species. Taurine plays an important role in the development of the central nervous system (CNS) and influences transportation procedures of divalent metal ions, e.g. as calcium, magnesium and zinc modulator. Taurine moreover acts as inhibiting neurotransmitter or neuromodulator. Relatively high concentrations of taurine are found in the CNS, in the retina and in the heart. It has been shown that taurine deficits may be involved in epilepsy, mongolism, diminished visual acuity and cardiac dysrhythmias. The taurine excretion is controlled by the kidneys, a taurine deficiency possibly leading to an abnormal development of the brain.

Surprisingly, it could also be shown that taurine assists and accelerates alcohol degradation within the body. By adding taurine to a composition which further comprises fructose and at least one vitamin B complex component, a drink is provided which degrades the alcohol within the body extremely effectively. These (at least) three components, if contained in a composition, surprisingly exhibit a synergistic effect, which means that the components functionally interact and in sum have a combinatory effect surpassing the sum of their individual activities. The combination of these (at least) three components has an extremely strong alcohol-degrading effect. Thereby the effects of an excessive alcohol consumption, e.g. headache, cardiovascular disturbances, thirst, nausea, tremor, vertigo, fatigue, impaired coordination etc. can be controlled much more effectively and rapidly than with the conventional, previously known means.

This drink composition may also be administered as an accompanying treatment in particularly extreme cases, such as in case of alcoholic poisoning accompanied by coma, circulatory breakdown, convulsions etc.

A further application is the treatment of alcoholics exhibiting chronic symptoms, such as chronic loss of electrolyte and loss of liquid, tremor, fatigue, impaired coordination, hyposthenia as well as mental problems, such as depressions, hallucinations etc.

A particularly suitable composition is provided in that it comprises fructose and components of the vitamin B complex in a weight ratio of from 10:1 to 10,000:1, in particular from 100:1 to 5,000:1, particularly preferably of 1,000:1. Even the two extreme ratios of 10:1 and 10,000:1 increase the degradation rate of blood alcohol, the ratio of fructose to components of the vitamin B complex of 1,000:1, however, has proven optimal for the accelerated alcohol degradation within the body.

Preferably, the components of the vitamin B complex are selected from the group consisting of vitamin B1, B2, B6, B12, biotin, niacin, pantothenic acid, folic acid, adenine, choline, adenosine phosphate, orotic acid, pangamic acid, carnitine, 4-aminobenzoic acid, myo-inositol, liponic acid and/or amygdaline. In the body, vitamin B1, also known as thiamin, is converted into thiamin-pyrophosphate, a coenzyme in a number of reactions in which C—C bonds are cleaved. It can, i.a., also be added as thiamin hydrochloride. Vitamin B2, also called riboflavin, is reabsorbed in the small intestines, converted into FMN (flavin mononucleotide) and, in the liver, into FAD (flavin-adenine-dinucleotide), both of which are coenzymes in redox reactions, i.a. with alcohol dehydrogenase. Vitamin B6, also called pyridoxal, pyrodoxin and pyridoxamine, is a component of pyridoxal-5-phosphate, which is a cofactor in glycogen degradation and in amino acid metabolism, e.g. as a coenzyme of decarboxylases. Prefeably, this substance is admixed to the drink compositon in the form of pyridoxin hydrochloride. Vitamin B12, also called cyanocobalamine, has a complex structure and is a component of cobalamine-coenzymes, with methylcobalamine and cobalamide, e.g., being involved i.a. in rearrangements with hydrogen migration. Biotin, also termed vitamin B7 or H. is covalently bound to carboxylases, niacin, a generic term for nicotinic acid and nicotin-amide, as a component of NAD and its phosphate, NADP, is one of the most important hydrogen transmitters in the cell and has a protective and anabolic effect on the body. Pantothenic acid, also called vitamin B3 or B5, respectively, has a precursor function for coenzyme A which assumes a central position in metabolism. Folic acid, or vitamin M, B9 or Bc, respectively, is a component of the coenzyme tetrahydrofolate. These examples given (to mention but a few) clearly show what an important role the vitamin B complex components play in metabolism.

Preferably, the refreshing drink composition comprises the components of the vitamin B complex in the following parts by weight, based on a total of 15,000–20,000 parts by weight of the dry substance: vitamin B1, 0.1–10, in particular 1; vitamin B2, 0.1–10, in particular 1.5; vitamin B6, 0.1–10, in particular 1.5, biotin, 0.01–1, in particular 0.1; niacin 0.1–100, in particular 10–30; pantothenic acid, 0.1–100, in particular 1–10; vitamin B12, 0.0001–0.1, in particular 0.001–0.01; and/or folic acid, 0.01–10, in particular 0.1. Of course, just a few (or only one) of these components may be contained in the composition, or the components may also have other ratios based on the dry substance weight. Many variations are possible, and with most variations an accelerated alcohol degradation is achieved. The preferred amounts mentioned here showed a particularly rapid degradation. Since the vitamin B complex components are water-soluble, any unused portion, if in excess, is excreted from the body. Accordingly, even at high concentrations of these components in the composition according to the invention, there is no risk of hypervitaminoses.

A particularly favorable result is obtained if the composition further comprises mineral substances, in particular magnesium and/or potassium and/or zinc. Since mineral substances are very important for a number of metabolic processes within the body, adding this group of substances to the composition of the beverage is important, it being possible to add several different mineral substances. In detail, zinc is a component of alcohol-dehydrogenase, potassium and magnesium play an important role in metabolism, magnesium i.a. being involved in all the ATP-catalyzed enzyme reactions. Mineral substances may be added in combination with further food additives, e.g. as magnesium glycerophosphate, potassium citrate (acid regulator), zink gluconate (fruit acid), calcium pantothenate, to mention but a few examples. Therefore, according to the invention it could be shown for the first time that activation of ADH (by zinc ions) and activation of the carbohydrate metabolism (by magnesium) directly lead to an accelerated alcohol degradation. So far, this has not been described or suggested in the literature.

Preferably, the composition comprises magnesium, potassium and/or zinc at the following parts by weight, based on a total of 15,000–20,000 parts by weight of the dry substance: magnesium, 10–1,000, in particular 100; potassium 10–1,000, in particular 100; zinc, 0.1–100, in particular 1–10. Also these amounts given are, of course, merely to be seen as guidelines, since various rations yield very good results. The amounts preferred here yielded the best results.

Furthermore, it is advantageous if the composition comprises amino acids, in particular L-glutamine and/or L-arginine. Amino acids play an important role in the various metabolic processes of the human body so that the addition of amino acids generally has a positive effect on the alcohol degradation of the body. Especially L-glutamine and L-arginine particularly promote alcohol degradation, and preferably they are admixed in the following parts by weight, based on a total of 15,000–20,000 parts by weight of dry substance: L-arginine, 20–2,000, in particular 200; L-glutamin, 10–1,000, in particular 100. These amounts yielded optimum alcohol degradation results.

Moreover, it is suitable if the composition comprises caffeine, in particular 0.1–100, particularly preferably 10–50 parts by weight, based on a total of 15,000–20,000 parts by weight of dry substance. Caffeine (theine, guaranine, trimethylxanthine) has a stimulating effect on the CNS, stimulates the cardiac activity, metabolism and breathing, the blood pressure, body temperature and blood circulation rate increase, the blood vessels in the brain dilate, while in the intestines they contract. This leads to a dispelling of fatigue, a transient improvement of the working performance and an elevation of the mood and counteracts the effects of alcohol.

Preferably, the refreshing drink composition preferably comprises anthocyans, in particular 0.1–100, particularly preferably 10 parts by weight, based on a total of 15,000–20,000 parts by weight of dry substance. Anthocyans are frequently used as colorants in the food industry, it being possible to obtain a red, blue or violet color, depending on the pH or on complex formation with metals.

Moreover, it is particularly advantageous if the composition comprises 10–1,000, preferably 100 parts by weight of taurine, based on a total of 15,000–20,000 parts by weight of dry substance. If taurine is added in this ratio, the optimum effect of taurine as well as an optimum synergistic effect of the combination product will be attained, resulting in an extremely effective and rapid alcohol degradation within the body, if this composition is ingested.

For an optimum alcohol degradation it is suitable if, based on 100 percent by weight of dry substance, the composition comprises 0.0001–0.1%, in particular 0.001–0.01%, each of B1, vitamin B2 and/or vitamin B6, 0.000001–0.001, in particular 0.00001–0.0001% of vitamin B12, 0.00001–0.01%, in particular 0.0001–0.001%, each of biotin and/or folic acid, 0.001–1%, in particular 0.01–0.1%, each of niacin, pantothenic acid, zinc and/or anthocyans, 0.01–10%, in particular 0.1–1%, each of magnesium, potassium, L-glutamine, caffeine and/or taurine, 0.01–100%, in particular 0.1–10%, of L-arginine, and/or 50–99.99%, in particular 95–98% of fructose. As mentioned above, various combinations are effective for increasing the alcohol degradation rate, yet these ratios mentioned here have proven to be optimal.

A further suitable composition is provided by adding further vitamins, in particular vitamin C. In this connection, all the vitamins common in food industry are possible, at the usual concentrations. Vitamin C is not necessary for increasing the alcohol degradation rate, it may, however be added, as is normally the case with drinks, in particular fruit juices, for health reasons (e.g. so as to support the immune defense).

Preferably, the composition comprises further additives, in particular flavoring agents, preserving agents, coloring agents, antioxidants, electrolytes, enzymes, plant extracts, glycerolphosphates, acid regulators and/or acidifiers, in particular fruit acids. In general, these substances have no particular influence on the alcohol degradation rate, they are merely added for food-technological reasons like in any other foodstuff and in drinks. As acid regulators, also antacids may be admixed which counteract an excessive acidification in the stomach, particularly after excessive wine consumption.

Further additional substances may also be histamines which counteract allergic reactions that occur in some persons to various ingredients of alcoholic drinks. Moreover, also quinines may be added, at least at low concentrations, which have a positive and accelerating effect on alcohol degradation and also are muscle relaxing.

A particularly preferred refreshing drink composition is also obtained in that it comprises further sugars and/or sweeteners. Both artificial and natural sweeteners may be added to sweeten the composition. Besides fructose, furthermore, any other sugar may be admixed, such as glucose, galactose, lactose etc. In this manner, the drink, besides the addition of fructose, will get a sweeter taste. Besides the sweetening effect, lactose also acts alcohol-degrading so that the content of alcohol will be further reduced by the addition of lactose.

The inventive refreshing drink of the initially defined type is characterized in that it further comprises a liquid foodstuff in addition to the above-described inventive composition. By dissolving/suspending the composition according to the invention with the liquid foodstuff, a liquid drink for lowering the blood alcohol level is obtained. Primarily, the liquid is water, and both carbonated and non-carbonated water may be used. Yet also any other liquid tolerable for the body may be added, such as, e.g., fruit juices, milk, tea, coffee and the like. Moreover, it is also possible to admix an alcohol-containing drink, e.g. an alcoholic cocktail, so that the alcohol-degrading effect will occur simultaneously with the alcohol consumption.

Furthermore, a composition according to the invention is provided which is present as a syrup or also as a dry substance. The syrup or the dry substance, respectively, may be diluted with or dissolved in any liquid tolerable for the body so as to obtain a drink that is as tasty as possible. The dry substance may, e.g, be prepared in the form of a powder or of tablets so that it is easy to handle and can be filled in portions into containers and can be taken along easily and used discretely. Furthermore, effervescent tablets or an effervescent powder which are easily soluble in the liquid and, on account of the carbonic acid, have a pleasant, prickling taste, are particularly easy to handle.

Of course, the invention also relates to any other possible consistency, wherein the alcohol-degrading composition containing at least fructose and vitamin B complex components may, of course, be ingested by drinking as well as by chewing, sucking, swallowing, to mention but a few examples.

The invention will be further explained by way of the following example and the drawing figures to which, of course, it is not restricted.

Figure 1:
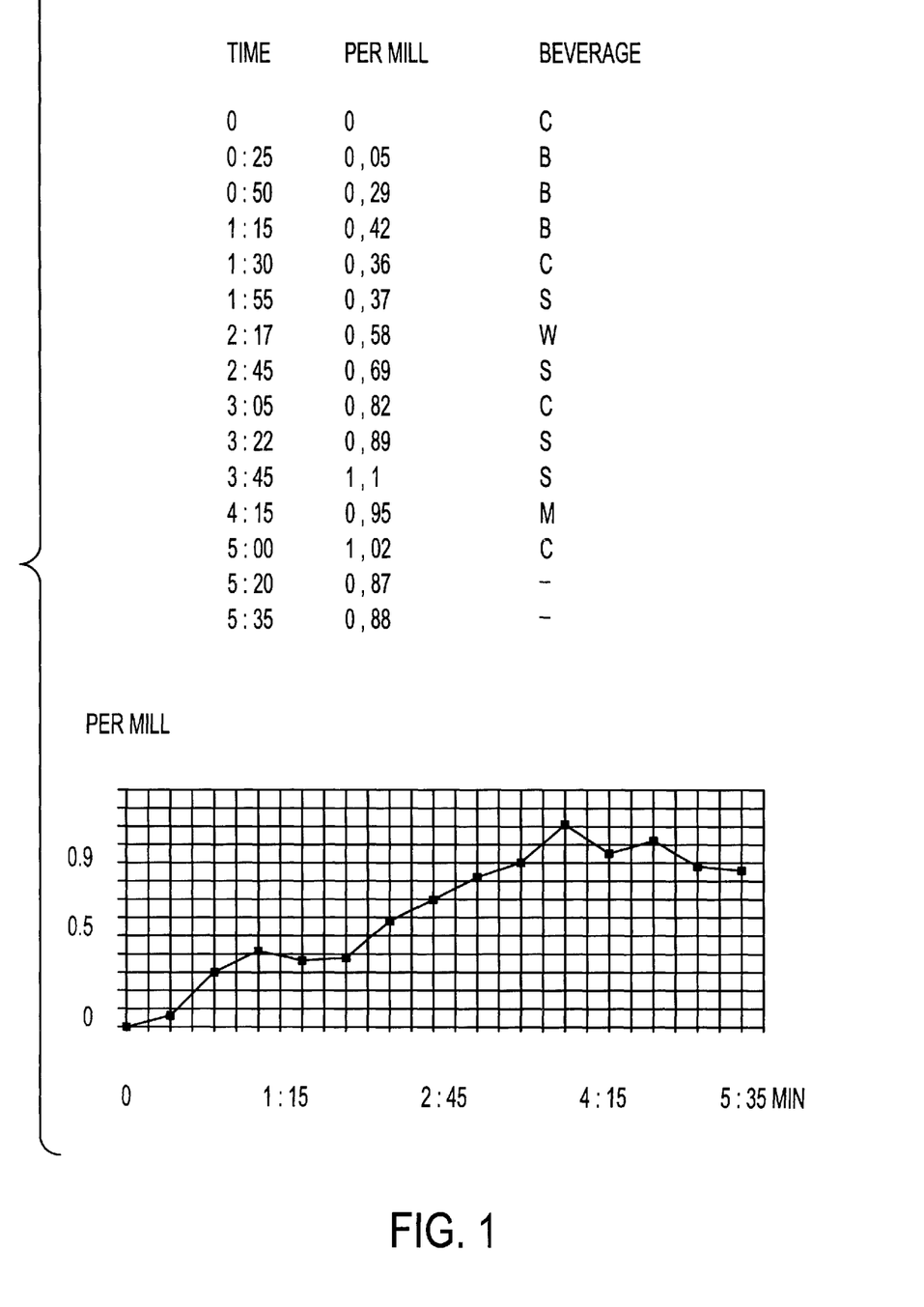
FIGS. 1–3 each show a verum test.
Figure 2:
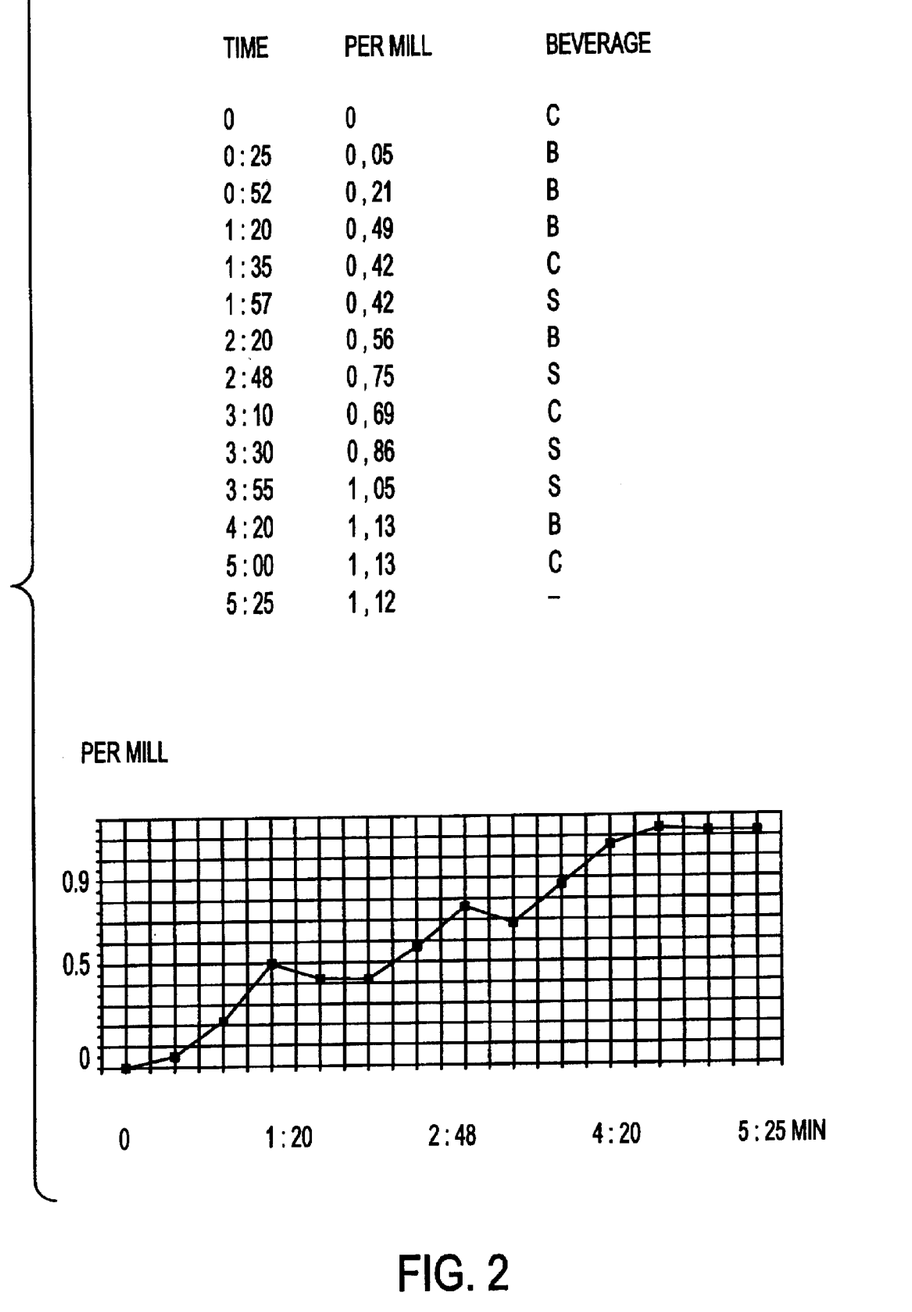
Figure 3:
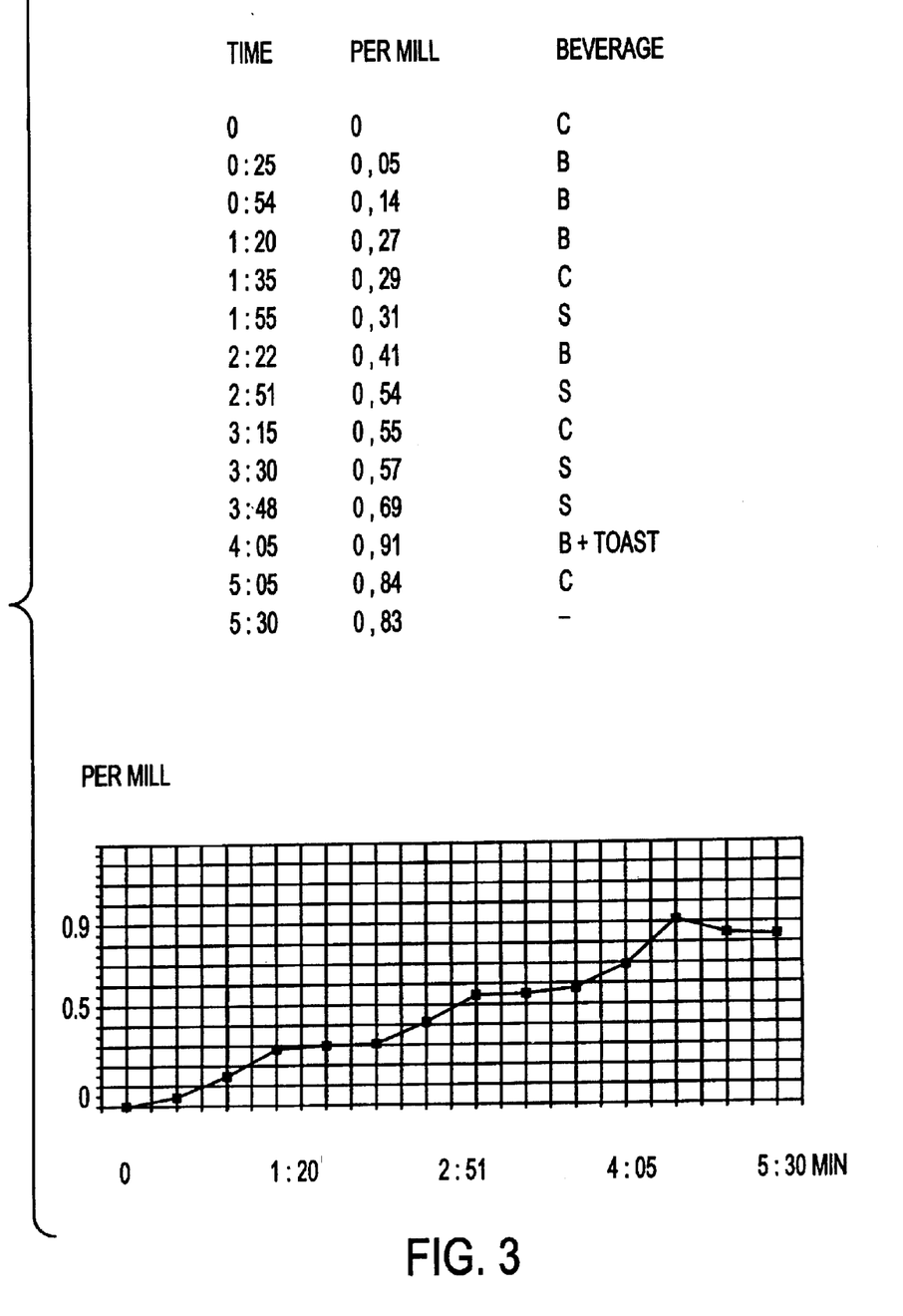
Figure 4:
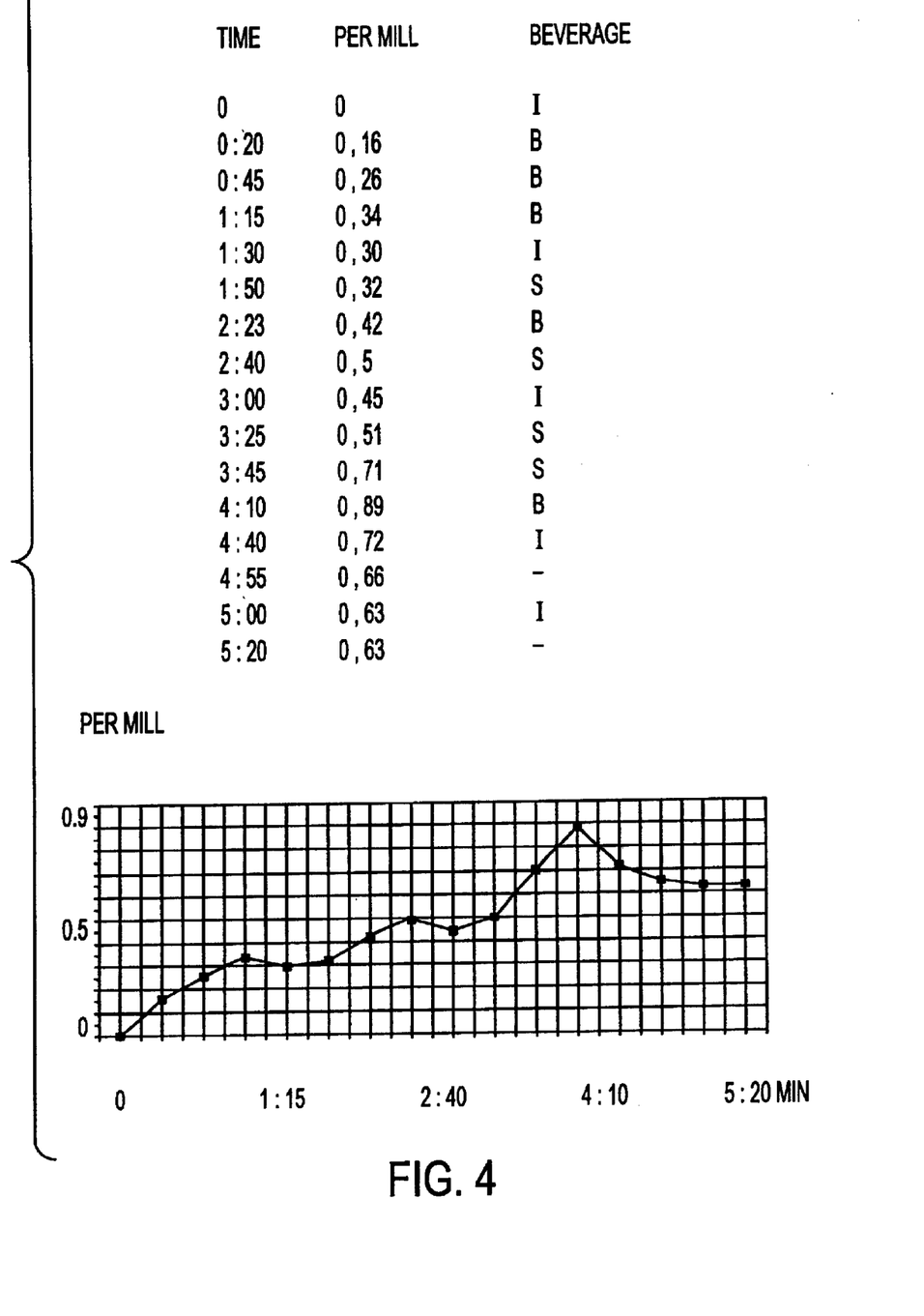
FIGS. 4–6 each show a placebo test, the per mill content of alcohol in time (min) being illustrated as a curve, and the individual results being listed in the table (I=drink according to the invention, S=spirits, B=beer, W=wine, C=Coca cola, M=mineral, –=no drink).
Figure 5:
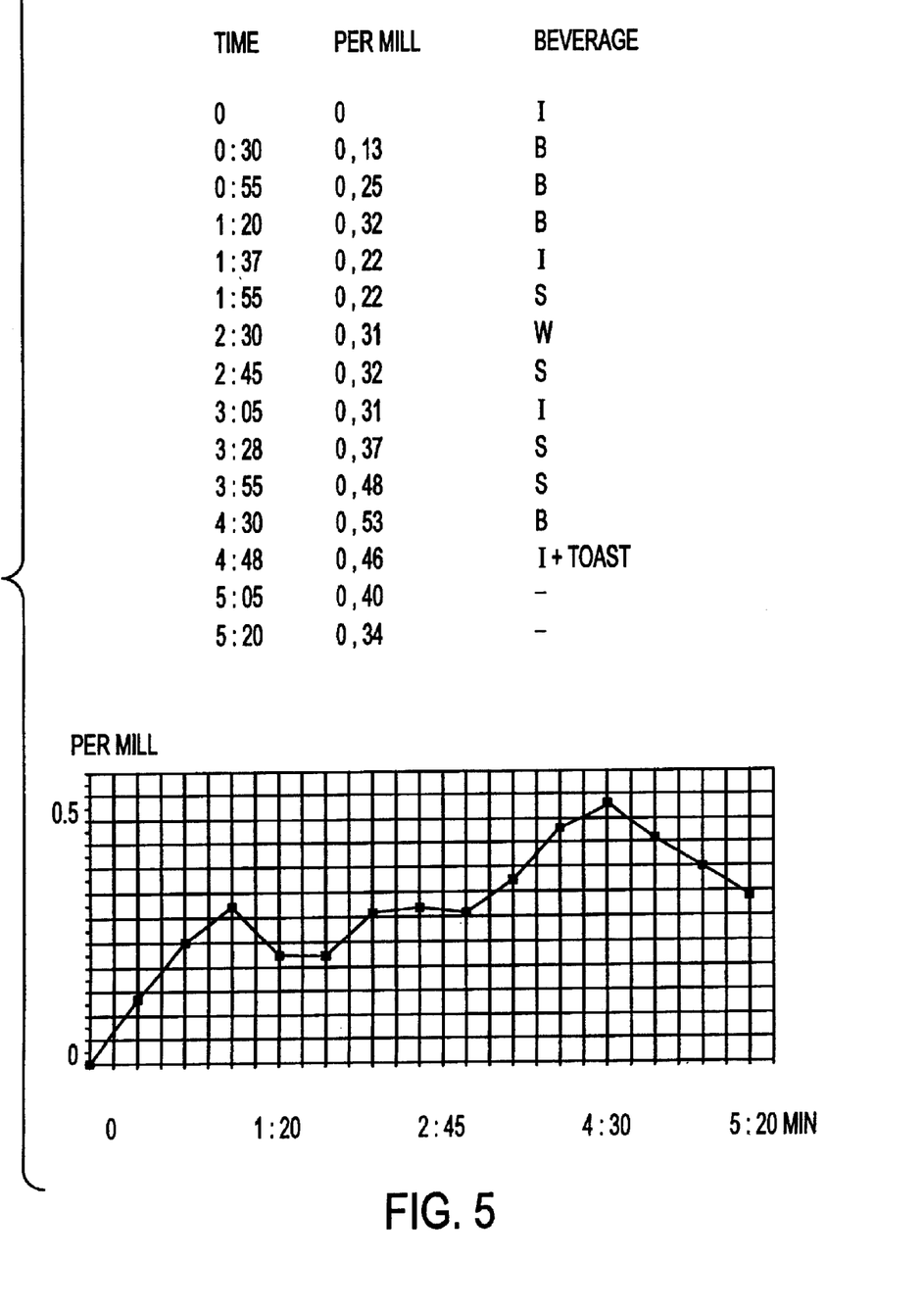
Figure 6:
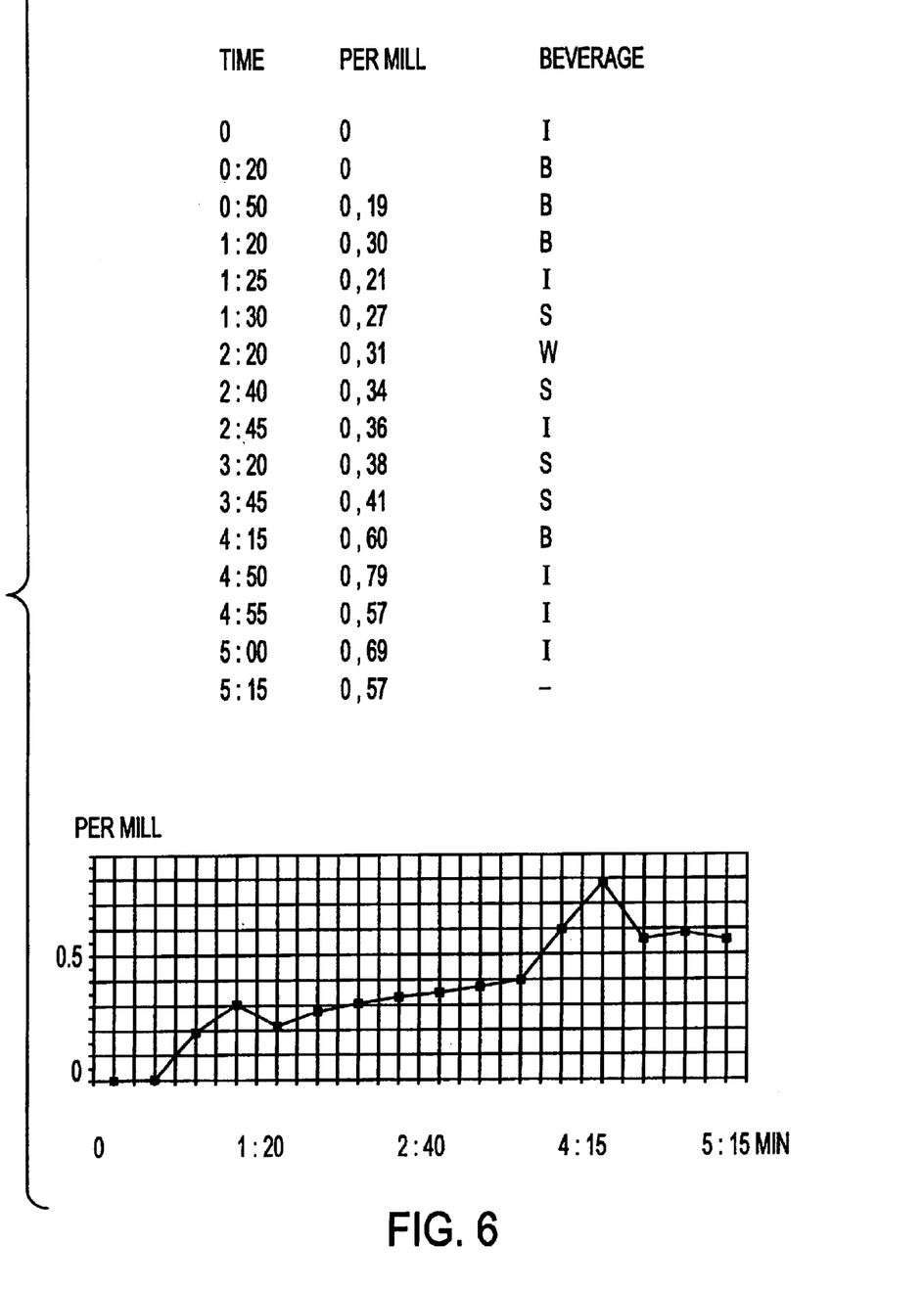

The following test persons have been used for the test: FIG. 1: female, born in 1975, 160 cm, 55 kg; FIG. 2: male, born in 1977, 175 cm, 68 kg; FIG. 3: male, born in 1968, 174 cm, 72 kg; FIG. 4: male, born in 1963, 178 cm, 85 kg; FIG. 5: male, born in 1957, 185 cm, 106 kg; FIG. 6: male, born in 1950, 180 cm, 82 kg. In the three verum tests (FIGS. 1–3), an increased alcohol degradation rate is clearly visible as compared to the placebo tests (FIGS. 4–6).

EXAMPLE

The following substances were added in 250 ml of water: 15 mg of niacin, 5 mg of pantothenic acid, 1.6 mg of vitamin B6, 1.5 mg of vitamin B2, 1.1 mg of vitamin B1, 0.1 mg of folic acid, 0.1 mg of biotin, 0.–2 μg of vitamin B12, 200 mg of L-arginine, 100 mg of L-glutamine, 100 mg of taurine, 100 mg of Mg, 100 mg of K, 5 mg of Zn, 100 mg of anthocyan, 30 mg of caffeine, 17,500 mg of fructose.

A participant group of 10 persons each received the same amount and type of alcohol (beer and spirits) over a period of 2.5 h. At the times 0; 60, 120 and 180 minutes, 5 persons received 250 ml each of the drink according to the invention (verum group), 5 persons each received 250 ml of a Coca Cola drink (control group). The measured alcohol levels were taken at 15 minute intervals over a period of 4 hours. The following day was spent with total alcohol abstinence. On the subsequent day, the previous test was repeated, yet this time the control group received the drink according to the invention, and the verum group received the Coca Cola drink.

The test persons were adult persons of either sex in good general health. Persons who had to take medicaments as a therapy as well as persons with liver and kidney dysfunctions were excluded as test participants. The measured alcohol values were determined from the respiratory air by means of the alcohol measuring device "Promillomat" licensed in Austria.

Results: The average alcohol degradation rate was 0.13% per hour in the control group, while it was 0.19% per hour in the verum group. This corresponds to an average increase in the alcohol degradation rate of 46% with the drink according to the invention. The calculated levels are arithmetic mean values.

What is claimed is:

1. A refreshing drink composition for increasing the alcohol degradation capacity of the body, said composition comprising fructose, at least one component of the vitamin B complex, and taurine.

2. A refreshing drink composition as set forth in claim 1, wherein said fructose and said vitamin B complex components are comprised in a weight ratio of from 10:1 to 10,000:1.

3. A refreshing drink composition as set forth in claim 1, wherein said fructose and said vitamin B complex components are comprised in a weight ratio of from 100:1 to 5,000:1.

4. A refreshing drink composition as set forth in claim 1, wherein said fructose and said vitamin B complex components are comprised in a weight ratio of 1,000:1.

5. A refreshing drink composition as set forth in claim 1, wherein said components of said vitamin B complex are selected from the group consisting of vitamin B1, B2, B6, B12, biotin, niacin, pantothenic acid, folic acid, adenine, choline, adenosine phosphat, orotic acid, pangamic acid, carnitine, 4-aminobenzoic acid, myo-inositol, liponic acid and amygdaline.

6. A refreshing drink composition as set forth in claim 1, said composition comprising said components of the vitamin B complex in parts by weight, based on a total of 15,000–20,000 parts by weight of the dry substance, selected from the group consisting of: vitamin B1, 0.1–10; vitamin B2, 01.1–10; vitamin B6, 0.1–10; biotin, 0.01–1; niacin, 0.1–100; pantothenic acid, 0.1–100; vitamin B12, 0.0001–0.1; and folic acid, 0.01–10.

7. A refreshing drink composition as set forth in claim 1, said composition comprising said components of the vitamin B complex in parts by weight, based on a total of 15,000–20,000 parts by weight of the dry-substance, selected from the group consisting of: vitamin B1, 1; vitamin B2, 1.5; vitamin B6, 1.5; biotin, 0.1; niacin, 10–30; pantothenic acid, 1–10; vitamin B12, 0.001–0.01 and folic acid, 0.1.

8. A refreshing drink composition as set forth in claim 1, further comprising mineral substances.

9. A refreshing drink composition as set forth in claim 8, wherein said mineral substances are at least one of magnesium, potassium and zinc.

10. A refreshing drink composition as set forth in claim 9, wherein said at least one of magnesium, potassium and zinc are comprised in parts by weight, based on a total of 15,000–20,000 parts by weight of dry substance, as follows: magnesium, 10–1,000; potassium, 10–1,000; zinc, 0.1–100.

11. A refreshing drink composition as set forth in claim 9, wherein said at least one of magnesium, potassium and zinc are comprised in parts by weight, based on a total of 15,000–20,000 parts by weight of dry substance, as follows: magnesium, 100; potassium, 100; zinc, 1–10.

12. A refreshing drink composition as set forth in claim 1, further comprising amino acids.

13. A refreshing drink composition as set forth in claim 12, wherein said amino acids are at least one of L-glutamine and L-arginine.

14. A refreshing drink composition as set forth in claim 13, wherein 20–2,000 parts by weight of L-arginine and 10–1,000 parts by weight of L-glutamine, based on a total of 15,000–20,000 parts by weight of dry substance, are comprised in said composition.

15. A refreshing drink composition as set forth in claim 13, wherein 200 parts by weight of L-arginine and 100 parts by weight of L-glutamine, based on a total of 15,000–20,000 parts by weight of dry substance, are comprised in said composition.

16. A refreshing drink composition as set forth in claim 1, further comprising caffeine.

17. A refreshing drink composition as set forth in claim 16, wherein 0.1–100 parts by weight of caffeine, based on a total of 15,000–20,000 parts by weight of dry substance, are comprised in said composition.

18. A refreshing drink composition as set forth in claim 16, wherein 10–50 parts by weight of caffeine, based on a total of 15,000–20,000 parts by weight of dry substance, are comprised in said composition.

19. A refreshing drink composition as set forth in claim 1, further comprising anthocyans.

20. A refreshing drink composition as set forth in claim 19, wherein 0.1–100 parts by weight of anthocyans, based on a total of 15,000–20,000 parts by weight of dry substance, are comprised in said composition.

21. A refreshing drink composition as set forth in claim 19, wherein 10 parts by weight of anthocyans, based on a total of 15,000–20,000 parts by weight of dry substance, are comprised in said composition.

22. A refreshing drink composition as set forth in claim 1, wherein 10–1,000 parts by weight of taurine, based on a total of 15,000–20,000 parts by weight of dry substance, are comprised in said composition.

23. A refreshing drink composition as set forth in claim 1, wherein 100 parts by weight of taurine, based on a total of 15,000–20,000 parts by weight of dry substance, are comprised in said composition.

24. A refreshing drink composition as set forth in claim 1, said composition comprising, based on 100% of dry substance, a substance selected from the group consisting of from 0.0001 to 0.1%, each of vitamin B1, vitamin B2 and vitamin B6, from 0.000001 to 0.001% of vitamin B12, from 0.00001 to 0.01% each of biotin and folic acid, from 0.001 to 1% each of niacin, pantothenic acid, zinc and anthocyans, from 0.01 to 10% each of magnesium, potassium, L-glutamine, caffeine and taurine, from 0.01 to 100% of L-arginine, and from 50 to 99.99% of fructose.

25. A refreshing drink composition as set forth in claim 1, said composition comprising, based on 100% of dry substance, a substance selected from the group consisting of from 0.001 to 0.01%, each of vitamin B1, vitamin B2 and vitamin B6, from 0.00001 to 0.0001% of vitamin B12, from 0.0001 to 0.001% each of biotin and folic acid, from 0.01 to 0.1% each of niacin, pantothenic acid, zinc and anthocyans, from 0.1 to 1% each of magnesium, potassium, L-glutamine, caffeine and taurine, from 0.1 to 10% of L-arginine, and from 95 to 98% of fructose.

26. A refreshing drink composition as set forth in claim 1, further comprising further vitamins.

27. A refreshing drink composition as set forth in claim 26, wherein said further vitamin is vitamin C.

28. A refreshing drink composition as set forth in claim 1, further comprising further additives.

29. A refreshing drink composition as set forth in claim 28, wherein said further additives are selected from the group consisting of flavoring agents, preserving agents, coloring agents, antioxidants, electrolytes, enzymes, plant extracts, glyccrolphosphates, acid regulators and acidifiers.

30. A refreshing drink composition as set forth in claim 29, wherein said acidifiers are fruit acids.

31. A refreshing drink composition as set forth in claim 1, further comprising at least one of further sugars and sweetners.

32. A refreshing drink composition for increasing the alcohol degradation capacity of the body, said composition comprising fructose, at least one component of the vitamin B complex, taurine, and a liquid foodstuff.

33. A refreshing drink composition as set forth in claim 1, said composition being provided as a syrup.

34. A refreshing drink composition as set forth in claim 1, said composition being provided as a dry substance.

35. A syrup for increasing the alcohol degradation capacity of the body, said syrup comprising fructose, at least one component of the vitamin B complex and taurine.

36. A dry substance for increasing the alcohol degradation capacity of the body, said dry substance comprising fructose, at least one component of the vitamin B complex and taurine.

37. A method of increasing the alcohol degradation capacity of an individual, said method comprising administering to said individual a fructose-containing refreshing drink composition, said composition further comprising at least one component of the vitamin B complex and taurine.

38. A method as set forth in claim 37, wherein said fructose and said components of the vitamin B complex are comprised at a weight ratio of from 10:1 to 10,000:1.

39. A method as set forth in claim 37, wherein said components of said vitamin B complex are selected from the group consisting of vitamin B1, B2, B6, B12, biotin, niacin, pantothenic acid, folic acid, adenine, choline, adenosine phosphate, orotic acid, pangamic acid, carnitine, 4-aminobenzoic acid, myo-inositol, liponic acid and anygdaline.

40. A method as set forth in claim 37, wherein said composition comprises said components of the vitamin B complex in parts by weight, based on a total of 15,000–20,000 parts by weight of the dry substance, selected from the group consisting of: vitamin B1, 0.1–10, vitamin B2, 0.1–10; vitamin B6, 0.1–10; biotin, 0.01–1; niacin, 0.1–100; pantothenic acid, 0.1–100, vitamin B12, 0.0001–0.1; and folic acid, 0.01–10.

41. A method as set forth in claim 37, wherein said composition further comprises mineral substances selected from the group consisting of magnesium, potassium and zinc.

42. A method as set forth in claim 41, wherein said mineral substances selected from the group consisting of magnesium, potassium and zinc are comprise parts by weight, based on a total of 15,000–20,000 parts by weight of dry substance, as follows: magnesium, 10–1,000; potassium, 10–1,000; zinc, 0.1–100.

43. A method as set forth in claim 37, wherein said composition further comprises amino acids selected from the group consisting of L-glutamine and L-arginine.

44. A method as set forth in claim 43, wherein 20–2,000 parts by weight of L-arginine and 10–1,000 parts by weight of L-glutamine, based on a total of 15,000–20,000 parts by weight of dry substance, are comprised in said composition.

45. A method as set forth in claim 37, wherein said composition further comprises caffeine.

46. A method as set forth in claim 45, wherein 0.10–100 parts by weight of caffeine, based on a total of 15,000–20,000 parts by weight of dry substance, are comprised in said composition.

47. A method as set forth in claim 37, wherein said composition further comprises anthocyans.

48. A method as set forth in claim 47, wherein 0.1–100 parts by weight of anthocyans, based on a total of 15,000–20,000 parts by weight of dry substance, are comprised in said composition.

49. A method as set forth in claim 37, wherein 10–1,000 parts by weight of taurine, based on a total of 15,000–20,000 parts by weight of dry substance, are comprised in said composition.

50. A method as set forth in claim 37, wherein said composition further comprises further vitamins.

51. A method as set forth in claim 37, wherein said further vitamin is vitamin C.

52. A method as set forth in claim 37, wherein said composition further comprises further additives selected from the group consisting of flavoring agents, preserving agents, coloring agents, antioxidants, electrolytes, enzymes, plant extracts, glycelolphosphates, acid regulators and acidifiers.

53. A method as set forth in claim 52, wherein said acidifiers are fruit acids.

54. A method as set forth in claim 37, wherein said composition further comprises at least one of further sugars and sweetners.

55. A method as set forth in claim 37, wherein said composition further comprises a liquid foodstuff.

56. A method as set forth in claim 37, wherein said composition is provided as a syrupy.

57. A method as set forth in claim 37, wherein said composition is provided as a dry substance.

* * * * *

UNITED STATES PATENT AND TRADEMARK OFFICE
CERTIFICATE OF CORRECTION

PATENT NO. : 6,514,544 B2  
DATED : February 4, 2003  
INVENTOR(S) : Fuchs et al.

It is certified that error appears in the above-identified patent and that said Letters Patent is hereby corrected as shown below:

<u>Title page,</u>  
Item [57], ABSTRACT,  
Line 3, please delete "contains" and insert -- comprises -- therefor.

<u>Column 7,</u>  
Line 62, please delete "phosphat" and insert -- phosphate -- therefor.

<u>Column 8,</u>  
Line 12, please insert -- ; -- between "0.01" and "and".

<u>Column 9,</u>  
Line 35, please delete "glyccrolphosphates" and insert -- glycerolphosphates -- therefor.

<u>Column 10,</u>  
Line 18, please delete "comprise" and insert -- comprised in -- therefor.  
Line 47, please delete "37" and insert -- 57 -- therefor.  
Line 53, please delete "glycelolphosphates" and insert -- glycerolphosphates -- therefor.  
Line 63, please delete "syrupy" and insert -- syrup -- therefor.

Signed and Sealed this

Fifteenth Day of April, 2003

JAMES E. ROGAN  
*Director of the United States Patent and Trademark Office*